United States Patent
Hakamata

(10) Patent No.: US 7,008,374 B2
(45) Date of Patent: Mar. 7, 2006

(54) IMAGING APPARATUS WHICH ADJUSTS FOR DARK NOISE AND READOUT NOISE

(75) Inventor: Kazuo Hakamata, Kaisei-machi (JP)

(73) Assignee: Fuji Photo Film Co., Ltd., Kanagawa-ken (JP)

(*) Notice: Subject to any disclaimer, the term of this patent is extended or adjusted under 35 U.S.C. 154(b) by 329 days.

(21) Appl. No.: 10/651,215

(22) Filed: Aug. 29, 2003

(65) Prior Publication Data

US 2004/0044275 A1 Mar. 4, 2004

(30) Foreign Application Priority Data

Aug. 30, 2002 (JP) ............................. 2002/254734
Jul. 30, 2003 (JP) ............................. 2003/282793

(51) Int. Cl.
*A61B 1/04* (2006.01)
*H04N 7/18* (2006.01)
*H04N 9/64* (2006.01)

(52) U.S. Cl. ..................... 600/109; 348/76; 348/241
(58) Field of Classification Search .................. 348/65, 348/76, 229.1, 230.1, 243, 297, 607; 600/109
See application file for complete search history.

(56) References Cited

U.S. PATENT DOCUMENTS

| 5,264,940 A | * | 11/1993 | Komiya et al. ............. 348/298 |
| 5,337,340 A | * | 8/1994 | Hynecek ...................... 377/60 |
| 6,760,058 B1 | * | 7/2004 | Hakamata .................... 348/45 |

FOREIGN PATENT DOCUMENTS

JP 7-176721 A 7/1995

* cited by examiner

*Primary Examiner*—John Leubecker
*Assistant Examiner*—Philip R. Smith
(74) *Attorney, Agent, or Firm*—Sughrue Mion, PLLC

(57) ABSTRACT

An imaging apparatus using a charge multiplying solid-sate imaging device for use with an endoscope system, etc., capable of providing an output signal with an improved S/N ratio by reducing the dark noise. The full well size of the CCD imaging device is reduced to 1/M of the number of electrons corresponding to a maximum amount of light which may be received by the individual pixel determined by the technical specifications of the system, and the signal charges are read out N times in a prescribed time period corresponding to a time for a single frame in a TV frame rate. The system satisfies the relation, nd $(1-1/M) > nr^2 (N^2-1)$, assuming that nd is the dark noise and nr is the readout noise contained in single reading from a reference solid-state imaging means having a full well size equivalent to the number of electrons described above.

10 Claims, 10 Drawing Sheets

IMAGING APPARATUS WHICH ADJUSTS FOR DARK NOISE AND READOUT NOISE

BACKGROUND OF THE INVENTION

1. Field of the Invention

The present invention relates to an imaging apparatus using a solid-state imaging means having a photoelectron multiplying section, and an image obtaining apparatus using the imaging apparatus.

2. Description of the Related Art

An imaging apparatus for picking up an optical image of an observation area using a solid-state imaging device, such as a CCD and the like, that converts the optical image to an electrical signal has been known. Recently, a charge multiplying solid-state imaging device has been developed. This type of imaging device multiplies signal charges obtained by the device based on a multiplication factor which is controlled by a multiplication factor control signal as described, for example, in Japanese Unexamined Patent Publication No. 7(1995)-176721. Thus, the mounting of this type of imaging device on an imaging apparatus may enhance and control the imaging sensitivity of the apparatus. More specifically, the use of this type of solid-sate imaging device allows the user to obtain an image under the condition in which the amount of light is insufficient for a conventional imaging device, and display it as a visible image, as well as appropriately controlling the imaging sensitivity in accordance with the imaging conditions. This type of charge multiplying solid-state imaging device having the charge multiplying means described above is called a CMD (Charge Multiplying Detector)—CCD, in which signal charges are multiplied by making use of the charge multiplication effect arising from the ionization caused by the collision of conduction electrons with atoms under a high intensity electric field.

In the charge multiplying solid-state imaging device, signal charges are multiplied at a stage prior to a charge detection circuit that sequentially converts the signal charges to a signal voltage, and outputs it as an output signal, so that readout noise generated in the charge detection circuit is not multiplied, thereby the signal-to-noise ratio of the output signal may be improved. Accordingly, the use of the charge multiplying solid-state imaging device with an imaging apparatus which needs to pick up an optical image under insufficient light for the image may improve the signal-to-noise ratio of the output signal.

Also, endoscope systems having a solid-state imaging device mounted thereon have been used widely. These systems have an advantage that a number of individuals may simultaneously observe an image obtained by the solid-state imaging device by displaying it on the monitor. In addition, the image can be displayed on the monitor as a highlighted image by processing it in various ways in advance, thereby greatly contributing to the progress in the medical services.

In recent years, the endoscope has been applied in the field of bronchial tube, otolaryngology, and joint, as well as a conventional field of digestive system, with an evolution toward a thinner endoscope. The thinner endoscope, however, limits the number of light guides carrying the illumination light, so that there may be a case in which a sufficient amount of light may not be irradiated. Thus, the development of an imaging apparatus capable of picking up an image with a desired imaging sensitivity has been anticipated. In addition, a fluorometric observation, in which the excitation light described above is irradiated on a living tissue, and the fluorescence generated by the tissue is observed, has also been practiced. The fluorescence generated by the living tissue is weak, so that there may be a case in which a fluorescent image may not be picked up. Therefore, the development of an imaging apparatus capable of picking up an image with a desired imaging sensitivity has been anticipated. The US Patent publication No. 20010743994 discloses an endoscope system having a charge multiplying solid-state imaging device mounted thereon for solving these problems.

The use of the charge multiplying solid-state imaging device reduces readout noise and results in an output signal with an improved signal-to-noise ratio. Meanwhile, the noise contained in the output data obtained by the charge multiplying solid-state imaging means is dominated by dark noise. Further, if an image is picked up under a high temperature, by a solid-state imaging means having a large full well size, or under the condition in which a long read time is required for the signal charges, the dark noise contained in the signal charges is multiplied. For this reason, in the charge multiplying solid-state imaging device, the dark noise contained in the signal charges are multiplied with the multiplication of the signal charges, so that the signal-to-noise ratio of the output signal may not be improved even if the readout noise is reduced.

It may be possible to cool the solid-state imaging device for this purpose. It is difficult, however, to provide a cooling device for the solid-state imaging device mounted, for example, on an endoscope which is to be inserted into a living body. Further, the endoscope has a problem that the dark noise is inevitably increased due to a temperature rise caused by the illumination light irradiated on the subject at the time of imaging.

SUMMARY OF THE INVENTION

The present invention has been developed in recognition of the circumstance described above, and it is an object of the present invention to provide an imaging apparatus using a charge multiplying solid-state imaging device capable of providing an output signal with an improved signal-to-noise ratio by reducing the noise.

The imaging apparatus according to the present invention comprises: a solid-state imaging means having a charge multiplying section for multiplying signal charges obtained through imaging by each of the pixels of the imaging means having a full well size equivalent to 1/M of the number of electrons corresponding to a maximum amount of light which may be received by the individual pixel determined by the technical specifications of the apparatus; and a reading means for reading out the signal charges from the solid-state imaging means N times in a predetermined time period, wherein the apparatus is adapted to satisfy the following relation:

$$nd(1-1/M) > nr^2(N^2-1)$$

where nd is the dark noise, and nr is the readout noise when signal charges are read out once in the predetermined time period from a reference solid-state imaging device with each of the pixels having a full well size equivalent to the number of electrons.

The term "full well size" means the number of electrons which may be stored in an individual pixel.

The term "number of electrons corresponding to a maximum amount of light which may be received by the individual pixel determined by the technical specifications of the apparatus" means the number of electrons corresponding to a maximum amount of light which may be received by the individual pixel of the solid-state imaging device determined by the illuminance of the imaging surface, frame rate, etc. that depend on the technical specifications of the apparatus, or the size, number of pixels, frame rate, etc., of the solid-state imaging device required by the technical specifications of the apparatus. Here the apparatus means an image obtaining apparatus that uses the imaging apparatus of the present invention, such as an endoscope system and the like.

The "predetermined time period" means a read time for a single frame in a general TV frame rate. More specifically, the TV frame rate in NTSC system is 30 frames/sec, and 25 frames/sec in PAL system, and 60 frames/sec in high definition TV (HDTV), so the predetermined time period may be 1/30 sec, 1/25 sec, or 1/60 sec.

In addition, the imaging apparatus according to the present invention may be an imaging apparatus adapted to further satisfy the following relation:

$$Nr^2/nd = 1/(2NM^2)$$

The image obtaining apparatus according to the present invention comprises: an irradiation means for guiding illumination light to an area under test and irradiating the light thereon; and an imaging apparatus of the present invention for picking up an optical image originating from the area by the irradiation of the illumination light from the irradiation means.

The image obtaining apparatus of the present invention may take the form of an endoscope having an insertion section comprising a part or whole of the irradiation means and imaging apparatus to be inserted into a living body. By doing so, the image obtaining apparatus of the present invention may be effectively used as an endoscope system.

DESCRIPTION OF THE PREFERRED EMBODIMENTS

Figure 1:
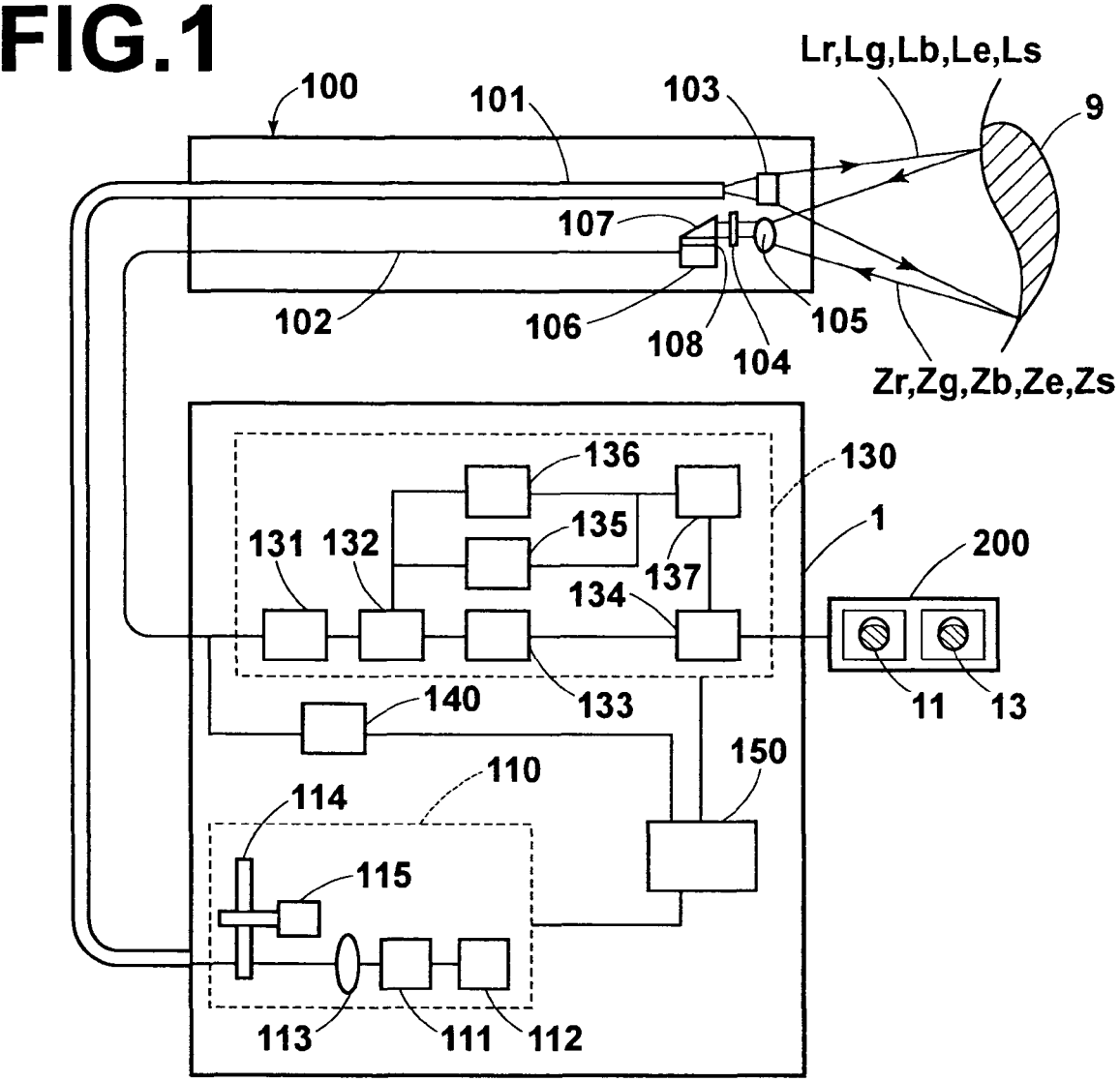
FIG. 1 is a schematic configuration diagram, illustrating the configuration of an endoscope system that uses an imaging apparatus according to a preferred embodiment of the present invention.

Hereinafter, a preferred embodiment of the present invention will be described with reference to the accompanying drawings. FIG. 1 is a schematic configuration diagram, illustrating the configuration of an endoscope system that uses an imaging apparatus according to a preferred embodiment of the present invention. As shown in FIG. 1, the endoscope system is a frame sequential endoscope in which illumination light of R-light (red) Lr, G-light (green) Lg, B-light (blue) Lb, reference light (near infrared light) Ls, and excitation light Le are irradiated sequentially on a living body observation area 9, and reflected images from the living body observation area 9 and a fluorescent image generated by the living body observation area 9 are picked up by a charge multiplying CCD imaging device, and subsequently displayed on the monitor as colored images. The endoscope system comprises an endoscope insertion section 100 to be inserted to an area of suspicious seat of disease of a patient, having a charge multiplying CCD imaging device at the leading end; an image data processing section 1 for processing image data representing the information obtained from the living body observation area 9; and a monitor 200 for displaying the image data processed by the image data processing section 1 as a visual image.

The endoscope insertion section 100 has therein a light guide 101 and a CCD cable 102 both extending to the end section thereof. An illumination optical system 103, excitation light cut filter 104, and converging lens 105 are disposed on the leading ends of the light guide 101 and CCD cable 102, i.e. at the leading end of the endoscope insertion section 100.

A mosaic filter 108 comprising microscopic band-pass filter elements combined in mosaic is connected to an on-chip charge multiplying CCD imaging device 106, and a prism 107 is attached thereto. The excitation light cut filter 104 is a long-pass filter that passes all the fluorescent light beams of wavelength not shorter than 420 nm. The other end of the light guide 101 opposite to the leading end is connected to an illumination unit 110, which will be described later. The CCD imaging device 106 picks up reflected images Zr, Zg, and Zb obtained by irradiating the R-light Lr, G-light Lg, and B-light Lb on the living body observation area 9, a fluorescent image Ze produced by the living body observation area 9 by the irradiation of the excitation light Le, and a reflected image Zs of the living body observation area 9 obtained by the irradiation of the reference light Ls; and converts these images into digital values to be outputted as the image data. (Zr, Zg, Zb, Ze, and Zs are hereinafter referred to as "optical images".)

Figure 2:
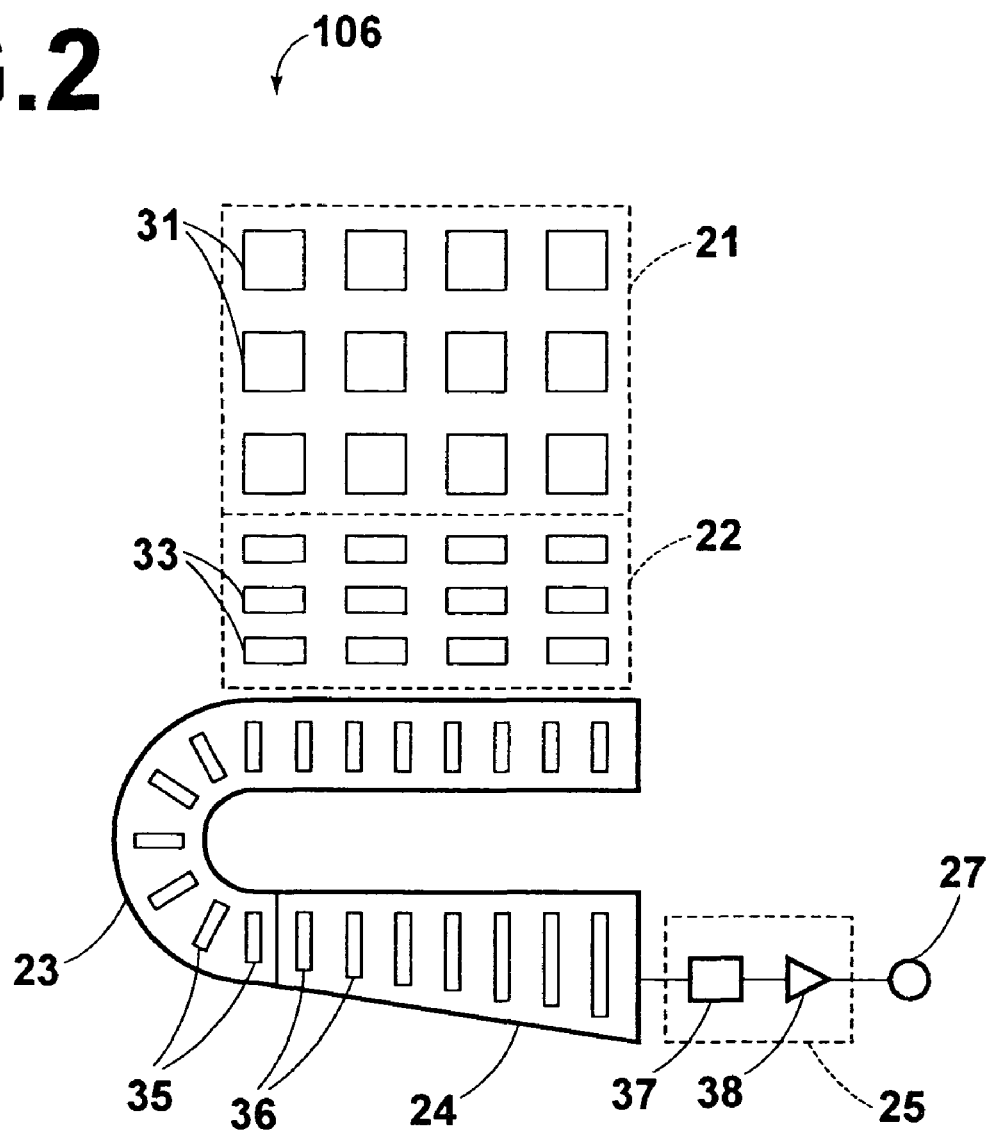
FIG. 2 is a drawing illustrating the configuration of a CCD imaging device.

FIG. 2 is a drawing illustrating the configuration of the CCD imaging device 106. As shown in FIG. 2, the CCD imaging device 106 is a frame transfer CMD-CCD imaging device, having a light receiving section 21 for converting an optical image received into signal charges; an storage section 22 for temporarily storing and transferring the signal charges; a horizontal transfer section 23 for horizontally transferring the signal charges; a charge multiplying section 24 for multiplying the signal charges based on a multiplication factor control signal input; and an output section 25 for converting the signal charges into a signal voltage which is amplified and outputted from an output terminal 27 to an image processing unit 130, which will be described later.

The light receiving section includes n pieces of vertical transfer CCDs 31 in the vertical direction, and n' pieces in the horizontal direction disposed in arrays for implementing photoelectric conversion and vertical transfer of the signal charges. The light receiving section 21 shown in FIG. 2 has 3 and 4 pieces of vertical transfer CCDs in the vertical and horizontal directions respectively to simplify the explanation. The actual CCD imaging device, however, has several hundreds of vertical transfer CCDs in both the vertical and horizontal directions.

The storage section 22 includes a plurality of vertical transfer CCDs 33 for temporary storage and vertical transfer of the signal charges, covered by a light shield made of, for example, a thin metal film. The horizontal transfer section 23 has a plurality of horizontal transfer CCDs 35.

The charge multiplying section 24 has m pieces of charge multiplying cells 36. The signal charges inputted to the charge multiplying section 24 are sequentially transferred through the section as they are multiplied based on a multiplication factor control signal, which is a sequential pulse signal. The charge multiplying cells 36 multiply the charges inputted by making use of the charge multiplication effect arising from the ionization caused by the collision of conduction electrons with atoms under a high intensity electric field, and output the multiplied charges. The multiplication factor depends on the signal characteristics of the multiplication factor control signal described above. In FIG. 2, the storage section 22, horizontal transfer section 23, and charge multiplying section 24 are illustrated in simplified form as is the light receiving section 21.

The output section 25 has a charge detecting section 37 for converting the signal charges into a signal voltage (output signal), and output amplifier 38 for amplifying the output signal.

In this preferred embodiment, the full well size of each of the pixels of the CCD imaging device 106 is determined to a size which is equivalent to 1/M of the number of electrons corresponding to the maximum amount of light which may be received by the individual pixel (hereinafter referred to as "number of electrons required by the apparatus") specified in the technical specifications of the apparatus, i.e., determined by the illuminance of the imaging surface, frame rate, etc. that depend on the technical specifications of the endoscope system, or the size, number of pixels, frame rate, etc. of the CCD imaging device 106 required by the technical specifications of the endoscope system, and the system reads out the signal charges N times in the predetermined time period. More specifically, the maximum number of electrons which may be stored in each of the pixels of the vertical transfer CCDs 33 of the CCD imaging device 106 is reduced to 1/M of the number of electrons required by the apparatus. The maximum number of electrons which may be stored in other CCDs than the vertical CCDs 33 may be reduced to 1/M of the number of electrons required by the system according to the pixel size, width of the charge transfer line, and the like. Hereinafter, the method for determining the values of M and N will be described.

Assuming that S is the strength of signal charges (hereinafter simply called as "output signal") obtained by single reading, nd is the dark noise, and nr is the readout noise of the CCD imaging device, in which each of the pixels has a full well size equivalent to the number of electrons required by the apparatus, the noise n0 contained in the output signal S may be expressed by the following Formula (1).

$$n0 = \sqrt{S + nr^2 + nd} \tag{1}$$

Here, the predetermined time period refers to the time period during which each of the light components having each color or wavelength band passes through a rotary filter 114, which will be described later, and is irradiated on the living body observation area 9 in one revolution of the filter. Hereinafter, the predetermined time period will be referred to as the prescribed read time. The apparatus according to this embodiment reads out the signal charges from the storage section 22 N times in every prescribed read time. Assuming that n1 is the noise contained in a signal obtained by each reading in N times of reading, the noise n1 is expressed by the following Formula (2).

$$n1 = \sqrt{\frac{S}{N} + (nr^2 \times N) + \frac{nd}{N}} \tag{2}$$

Accordingly, the noise n1' contained in a cumulated signal obtained by accumulating the signals read out through N times of reading is expressed by the following Formula (3).

$$n1' = \sqrt{\sum_n n1^2} = n1 \times \sqrt{N} \tag{3}$$

$$= \sqrt{\frac{S}{N} + (nr^2 \times N) + \frac{nd}{N}} \times \sqrt{N}$$

$$= \sqrt{S + nr^2 \times N^2 + nd}$$

Further, in this embodiment, each of the pixels of the CCD imaging device 106 has a full well size equivalent to 1/M of the number of electrons required by the apparatus. The noise n2 contained in a signal obtained by each reading in N times of reading during the prescribed read time using the CCD imaging device 106 described above is expressed by the following Formula (4).

$$n2 = \sqrt{\frac{S}{N} + (nr^2 \times N) + \frac{nd}{N \times M}} \tag{4}$$

Accordingly, the noise ni contained in a cumulated signal obtained by accumulating N signals, each obtained by each reading, is expressed by the following Formula (5).

$$ni = \sqrt{S + nr^2 \times N^2 + \frac{nd}{M}} \tag{5}$$

Here, in this preferred embodiment, the amount of noise contained in the cumulated signal obtained by the CCD imaging device with each of the pixels having a full well size equivalent to 1/M of the number of electrons required by the apparatus, in which the signal charges are read out N times in every prescribed read time needs to be smaller than that contained in a cumulated signal obtained by the CCD imaging device with each of the pixels having a full well size equivalent to the number of electrons required by the apparatus, in which the signal charges are read out once in every prescribed read time, i.e., n0>ni. Hence, $$\sqrt{S + nr^2 + nd} > \sqrt{S + nr^2 \times N^2 + \frac{nd}{M}} \quad (6)$$

The Formula (6) above may be rewritten as $$nr^2 + nd > nr^2 \times N^2 + \frac{nd}{M} \quad (7)$$

$$nd\left(1 - \frac{1}{M}\right) > nr^2(N^2 - 1)$$

Thus, by setting the values of M and N to satisfy the relation expressed by the Formula (7), the signal-to-noise ratio of the cumulative signal obtained by the apparatus according to this preferred embodiment may be improved.

Next, the conditions of M and N for minimizing the noise contained in the signal will be discussed. When Formula (5) is differentiated with respect to M and N, then $$\frac{dni}{dM} = \frac{d}{dM}\sqrt{S + nr^2 \cdot N^2 + \frac{nd}{M}} \quad (8)$$

$$= \frac{-1}{\left[2 \cdot \left(S + nr^2 \cdot N^2 + \frac{nd}{M}\right)^{\left(\frac{1}{2}\right)}\right]} \cdot \frac{nd}{M^2}$$

$$\frac{dni}{dN} = \frac{d}{dN}\sqrt{S + nr^2 \cdot N^2 + \frac{nd}{M}} \quad (9)$$

$$= \frac{1}{\left(S + nr^2 \cdot N^2 + \frac{nd}{M}\right)^{\left(\frac{1}{2}\right)}} \cdot nr^2 \cdot N$$

The formula above can be rewritten as $$\frac{1}{2} \cdot \frac{(-nd + 2 \cdot nr^2 \cdot N \cdot M^2)}{\left[\left[\frac{(S \cdot M + nr^2 \cdot N^2 \cdot M + nd)}{M}\right]^{\left(\frac{1}{2}\right)} \cdot M^2\right]} = 0 \quad (11)$$

$$\frac{1}{2} \cdot \frac{(-nd + 2 \cdot nr^2 \cdot N \cdot M^2)}{\left[\left[\frac{(S \cdot M + nr^2 \cdot N^2 \cdot M + nd)}{M}\right]^{\left(\frac{1}{2}\right)} \cdot M^2\right]} = 0 \quad (10)$$

Here, the denominator is always greater than 0, the numerator=0, or the following needs to be satisfied.

$$0 = nd + 2 \cdot nr^2 \cdot N \cdot M^2 \quad (12)$$

Therefore, the amount of noise is minimized when $$\frac{nr^2}{nd} = \frac{1}{2N \cdot M^2} \quad (13)$$

Noise characteristics obtained by changing M and N in various values are shown in FIGS. 3 to 6. In FIGS. 3 to 6, the vertical axis indicates the amount of noise per pixel (unit: e−, reference symbol: n4i), and the values indicate an amount of signal (e−), readout noise (e−), device temperature (° C.), exposure time (sec), prescribed read time (sec), N, and M. The value 10 in the vertical axis indicates the amount of output noise per pixel for single reading in the prescribed read time indicated in the Figure using the CCD imaging device with each pixel having a full well size equivalent to the number of electrons required by the apparatus.

Figure 3:
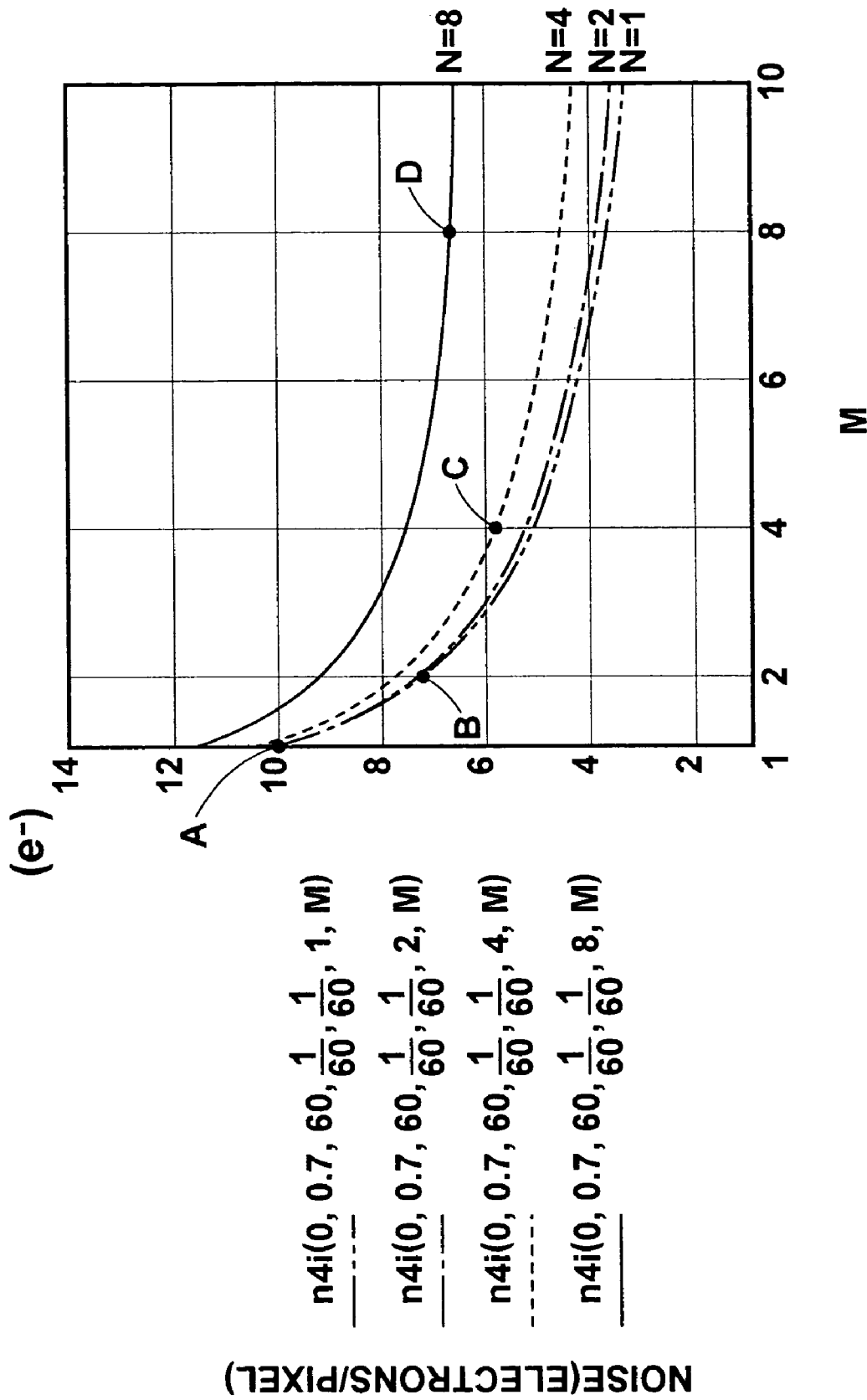
FIG. 3 is a drawing illustrating noise characteristics obtained by changing the values of M and N (case 1).

FIG. 3 shows the noise characteristics obtained by changing M in various values under the conditions in which the readout noise is set at 0.7 e−, device temperature at 60° C., exposure time at 1/60 sec, prescribed read time at 1/60 sec, and reading frequency N at 1, 2, 4, and 8 times in every prescribed read time of 1/60 sec. In the case of N=2, 4, and 8, in order to obtain an identical signal to that obtained by the single reading in every prescribed read time of 1/60 sec using a CCD imaging device with each pixel having a full well size equivalent to the number of electrons required by the system, i.e., in the case of N=1 and M=1, the value M needs to be set at 2 when N=2, 4 when N=4, and 8 when N=8. Dots A, B, C, and D indicate the amount of noise when N=1 and M=1, N=2 and M=2, N=4 and M=4, and N=8 and M=8 respectively. In FIG. 3, the noise is reduced to a minimum when N=4 and M=4.

Figure 4:
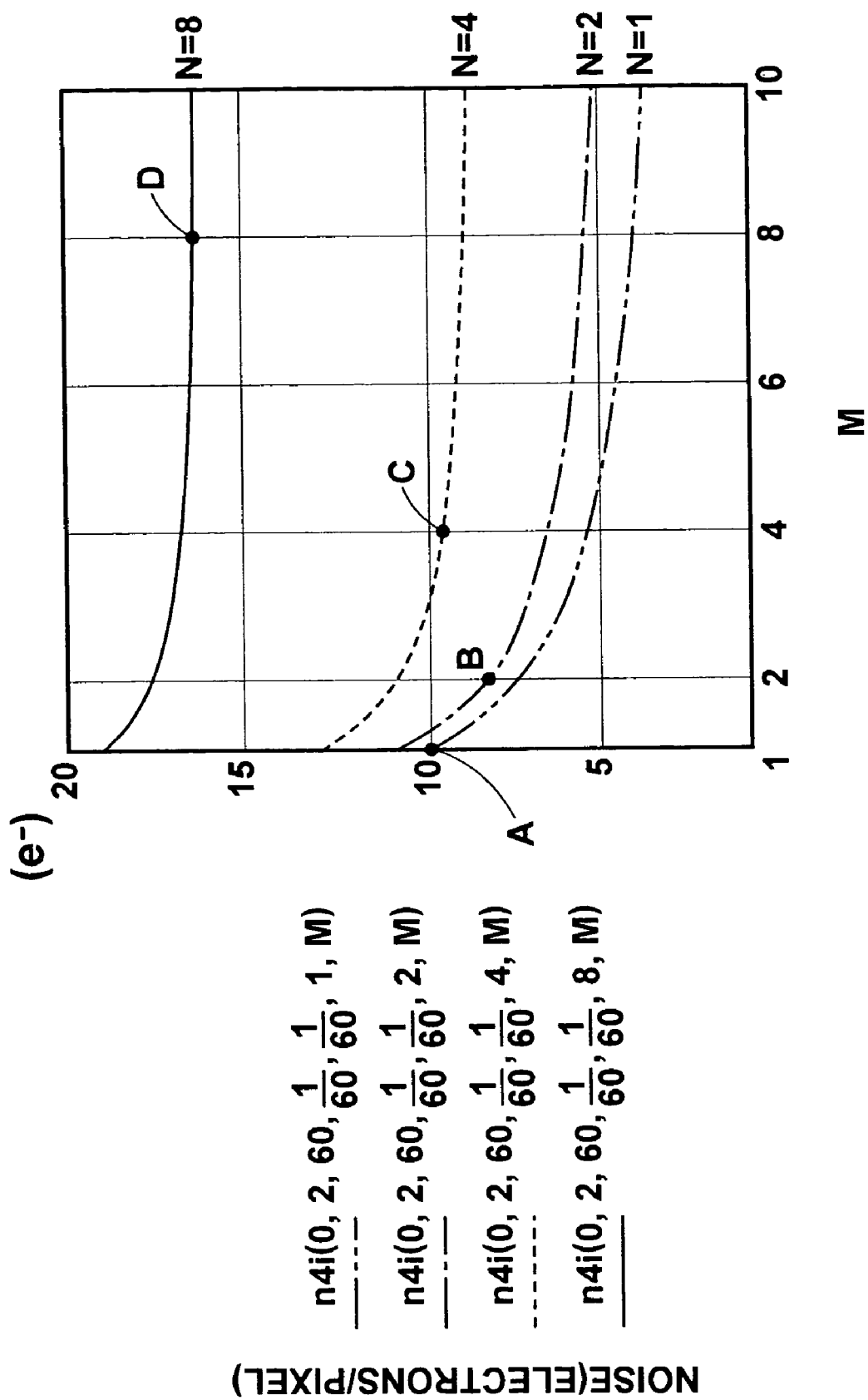
FIG. 4 is a drawing illustrating noise characteristics obtained by changing the values of M and N (case 2).

FIG. 4 shows the noise characteristics obtained by changing M in various values under the conditions in which the readout noise is set at 2 e−, device temperature at 60° C., exposure time at 1/60 sec, prescribed read time at 1/60 sec, and reading frequency N at 1, 2, 4, and 8 times in every prescribed read time of 1/60 sec. In the case of N=2, 4, and 8, in order to obtain an identical signal to that obtained in the case of N=1 and M=1, the value M needs to be set at 2 when N=2, 4 when N=4, and 8 when N=8. Dots A, B, C, and D indicate the amount of noise when N=1 and M=1, N=2 and M=2, N=4 and M=4, and N=8 and M=8 respectively. In FIG. 4, the noise is reduced to a minimum when N=2 and M=2.

Figure 5:
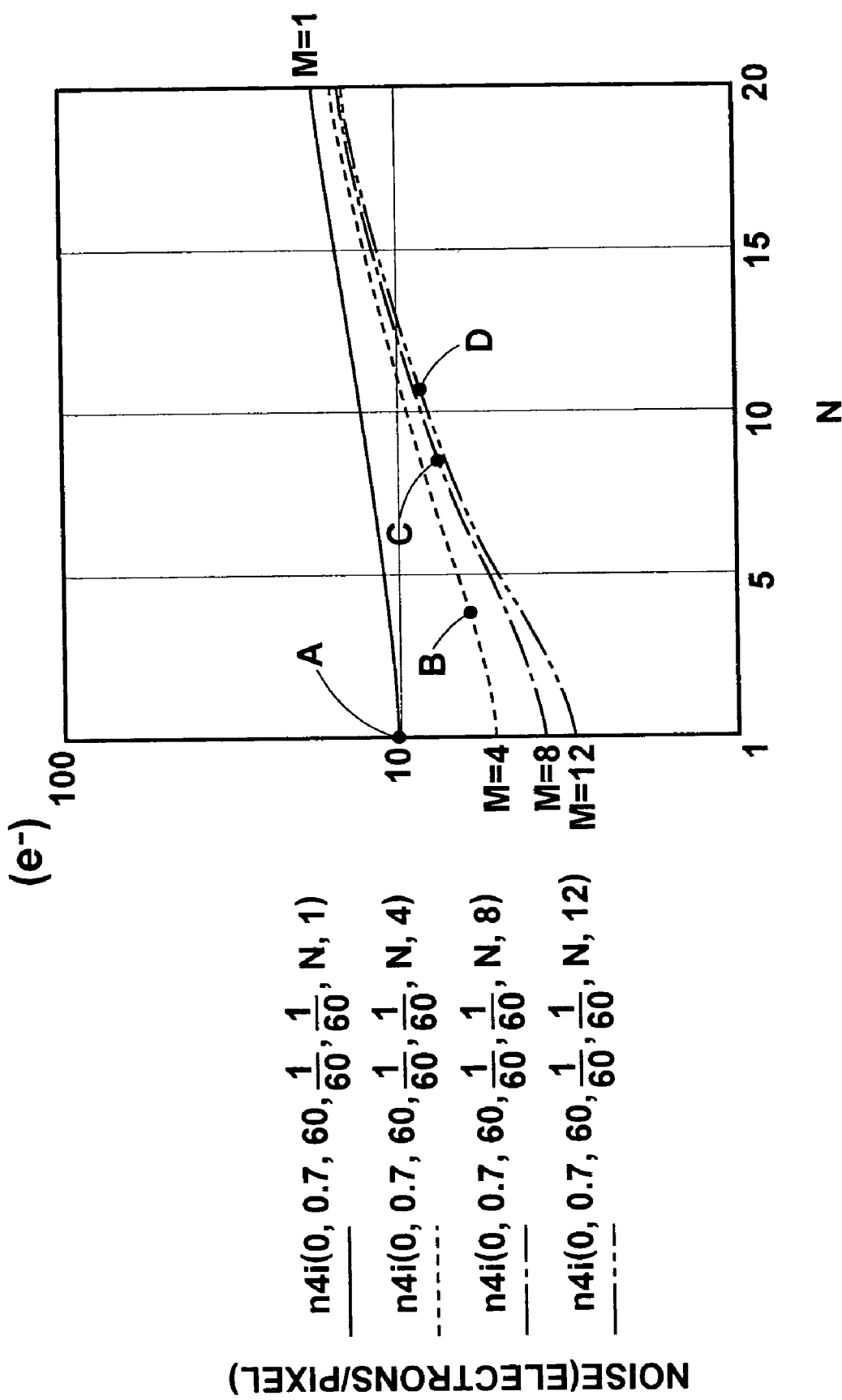
FIG. 5 is a drawing illustrating noise characteristics obtained by changing the values of M and N (case 3).

FIG. 5 shows the noise characteristics obtained by changing reading frequency N in every prescribed read time in various values under the conditions in which the readout noise is set at 0.7 e−, device temperature at 60° C., exposure time at 1/60 sec, prescribed read time at 1/60 sec, and the value of M at 1, 4, 8, and 12. In the case of M=4, 8 and 12, in order to obtain an identical signal to that obtained in the case of N=1 and M=1, the value N needs to be set at 4 when M=4, 8 when M=8, and 12 when M=8. Dots A, B, C, and D indicate the amount of noise when N=1 and M=1, N=4 and M=4, N=8 and M=8, and N=12 and M=12 respectively. In FIG. 5, the noise is reduced to a minimum when N=4 and M=4.

Figure 6:
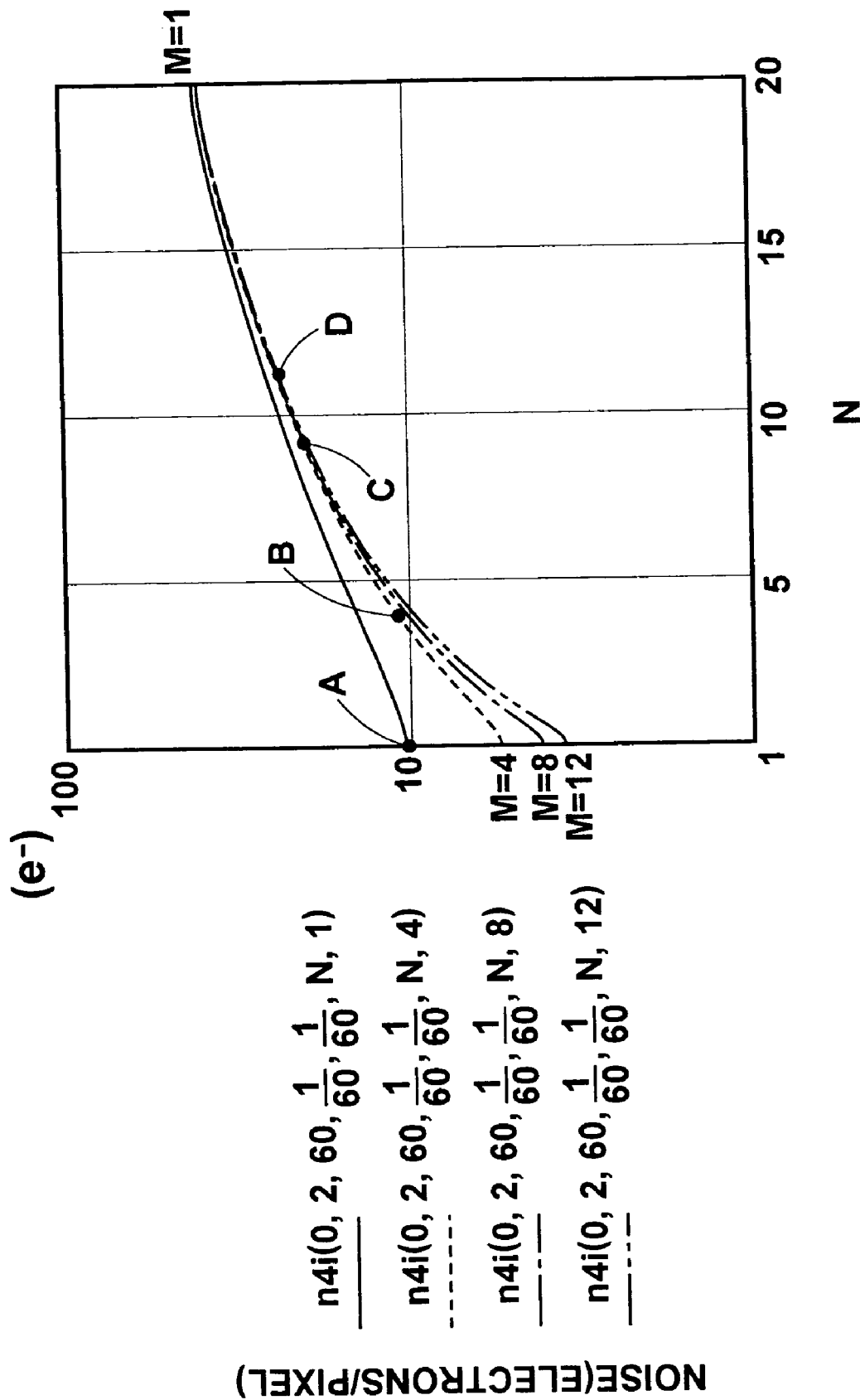
FIG. 6 is a drawing illustrating noise characteristics obtained by changing the values of M and N (case 4).

FIG. 6 shows the noise characteristics obtained by changing reading frequency N in every prescribed read time in various values under the conditions in which the readout noise is set at 2 e−, device temperature at 60° C., exposure time at 1/60 sec, prescribed read time at 1/60 sec, and the value of M at 1, 4, 8, and 12. In the case of M=4, 8 and 12, in order to obtain an identical signal to that obtained in the case of N=1 and M=1, the value N needs to be set at 4 when M=4, 8 when M=8, and 12 when M=8. Dots A, B, C, and D indicate the amount of noise when N=1 and M=1, N=4 and M=4, N=8 and M=8, and N=12 and M=12 respectively. In FIG. 6, the noise is reduced to a minimum when N=1 and M=1 or N=4 and M=4.

The comparison between FIGS. 3 and 4, or between FIGS. 5 and 6 shows that the smaller the amount of readout noise is, the less amount of output noise may result, when the values of M and N are set to obtain an identical signal to that obtained by the single reading using a CCD imaging device with each of the pixels having a full well size equivalent to the number of electrons required by the apparatus, i.e., in the case of N=1 and M=1 under the same temperature, exposure time, and prescribed read time.

Hereinafter, the noise characteristic of this preferred embodiment taking into account the readout noise and temperature will be described. Assuming that the dark noise per pixel per second at 21° C. is nd21, the dark noise nd(T) per pixel per second of the CCD imaging device 106 used in this preferred embodiment at a given temperature T is expressed as $$nd(T) = nd21 \cdot 2^{\frac{T-21}{8}} \qquad (14)$$

Figure 7:
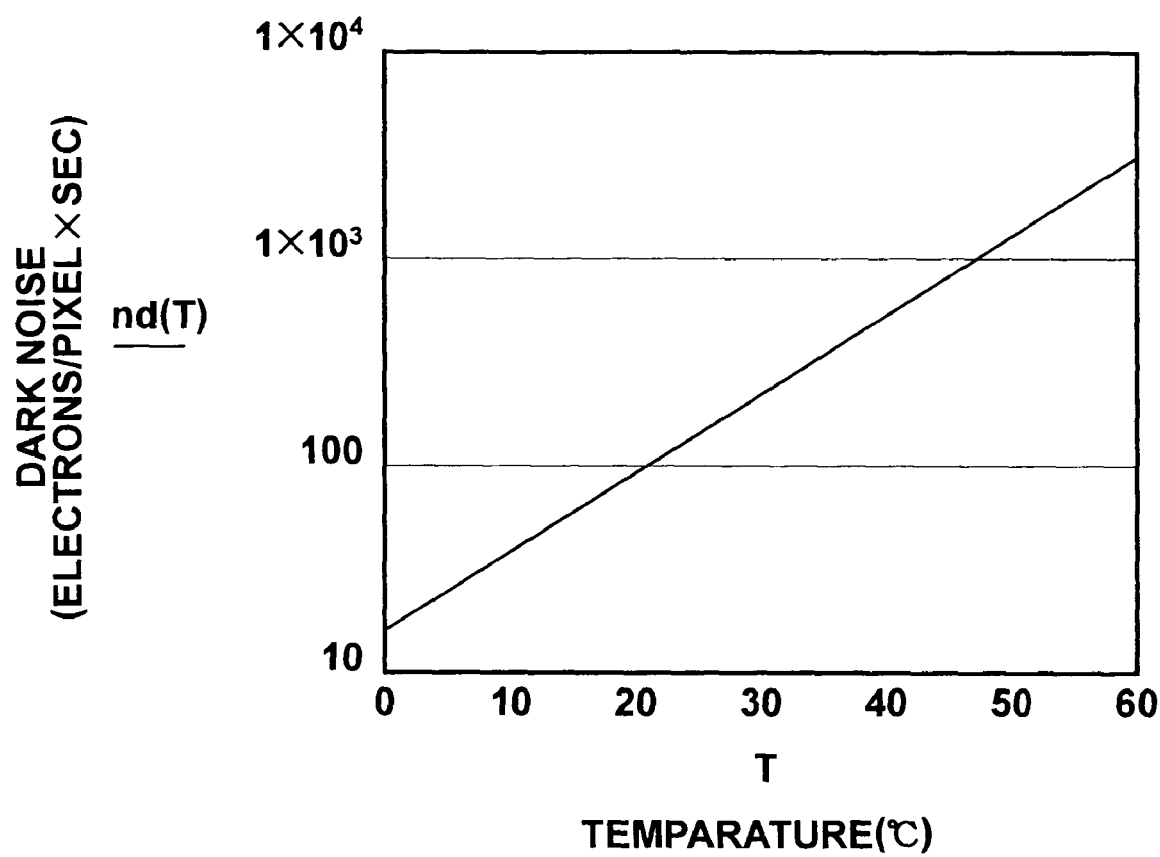
FIG. 7 is a drawing illustrating the relationship between the temperature and dark noise of a CCD imaging device used in a preferred embodiment of the present invention.

The relationship between the temperature and dark noise nd(T) of the CCD imaging device used in this preferred embodiment is shown in FIG. 7.

Meanwhile, assuming that the exposure time is texp, and the prescribed read time is tread, the dark noise nd(T, texp, tread) at the temperature T is expressed as $$nd(T, texp, tread) = nd(T) \cdot (texp + tread) \qquad (15)$$

The Formula (15) is substituted into the Formula (14) above to obtain $$n2 = \sqrt{\frac{S}{N} + (nr^2 \times N) + \frac{nd(T, texp, tread)}{N \times M}} \qquad (16)$$

Figure 8:
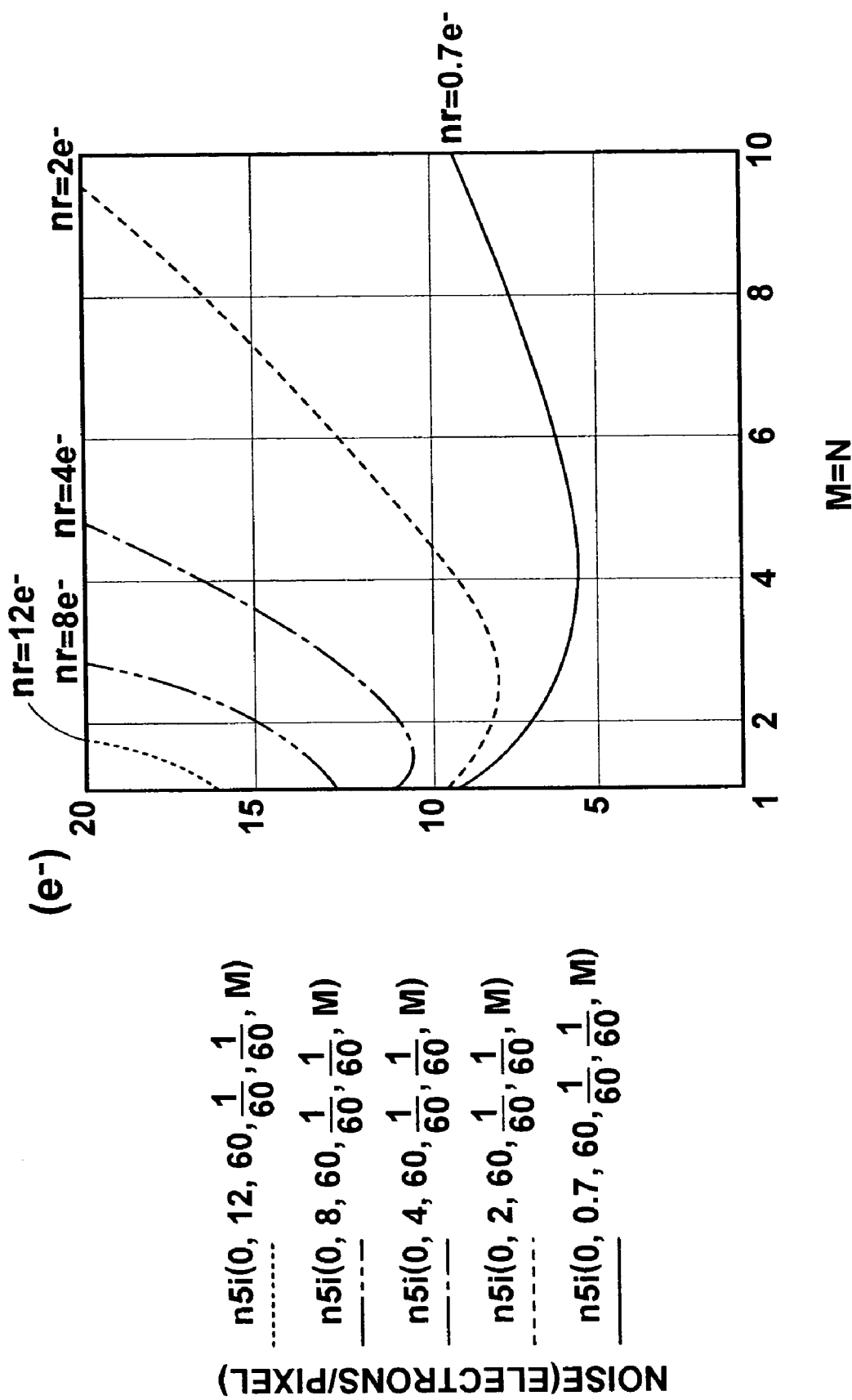
FIG. 8 is a drawing illustrating noise characteristics taking into account the readout noise and temperature (case 1)
Figure 9:
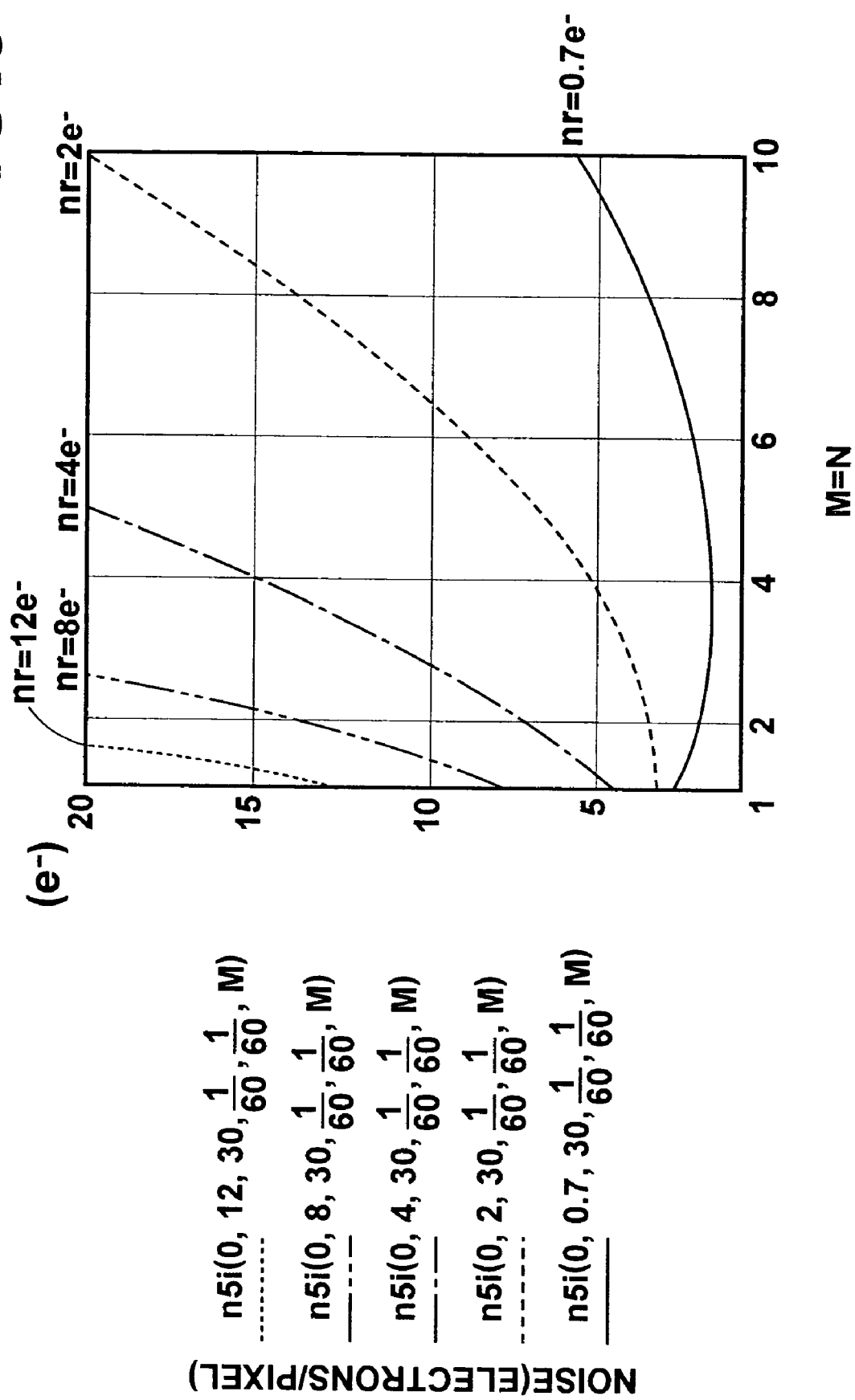
FIG. 9 is a drawing illustrating noise characteristics taking into account the readout noise and temperature (case 2)

The noise characteristics taking into account the readout noise and temperature based on the Formula (16) are shown in FIGS. 8 and 9. In FIGS. 8 and 9, the value M is set equal to that of N (M=N), and the vertical axis indicates the amount of noise per pixel (unit: e⁻, reference symbol: n5i), and the values indicate an amount of signal (e⁻), readout noise (e⁻), device temperature (° C.), exposure time (sec), prescribed read time (sec), and M(=N). The value 10 in the vertical axis indicates the amount of output noise per pixel for the single reading using a CCD imaging device with each of the pixels having a full well size equivalent to the number of electrons required by the system.

FIG. 8 shows the noise characteristics obtained by changing M(=N) in various values under the conditions in which the device temperature is set at 60° C., exposure time at ⅟₆₀, prescribed read time at ⅟₆₀ sec, and readout noise at nr=0.7, 2, 4, 8, and 12. FIG. 9 shows the noise characteristics obtained by changing M(=N) in various values under the conditions in which the device temperature is set at 30° C., exposure time at ⅟₆₀, prescribed read time at ⅟₆₀ sec, and readout noise at nr=0.7, 2, 4, 8, and 12.

The comparison between FIGS. 8 and 9 indicates that when the device temperature is high (60° C.), i.e., under the condition in which a larger amount of dark noise is present, the noise reduction effect according to this preferred embodiment is greater, if the amount of readout noise is small, like 0.7 e⁻.

Figure 10:
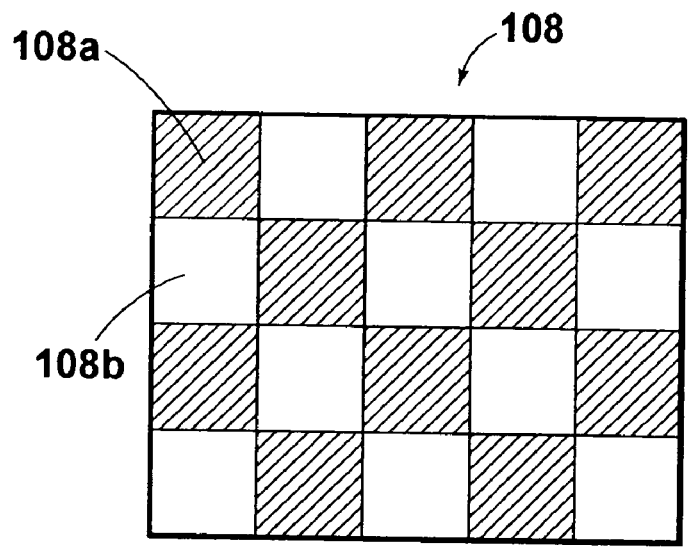
FIG. 10 is a drawing illustrating the configuration of a mosaic filter.

FIG. 10 is a drawing illustrating the configuration of a mosaic filter 108. As illustrated in the FIG. 10, the mosaic filter 108 comprises wide band-pass filer elements 108a that pass the light component in the wavelength range from 400 nm to 900 nm, and narrow band-pass filter elements 108b that pass the light component in the wavelength range from 430 nm to 530 nm, alternately interlaced with each other. Each of the band-pass filter elements 108a and 108b corresponds to each of the pixels of the CCD imaging device 106 in one-to-one relationship.

Image data processing section 1 comprises an illumination unit 110 for irradiating illumination light; an image processing unit 130 for processing image data to be displayed as an image; a CCD controller for controlling the operation of the CCD imaging device 106; and a controller 150 for implementing controls between each unit and the CCD controller 140.

The illumination unit 110 comprises a white light source 111 of xenon lamp that radiates white light; a light source power supply 112 electrically connected to the white light source 111; a converging lens 113 for converging the while light radiated from the white light source 111; a rotary filter 114 for sequentially separating the colors of the white light into R-light, G-light, B-light, reference light, and excitation light; and a motor 115 for rotating the rotary filter 114.

Figure 11:
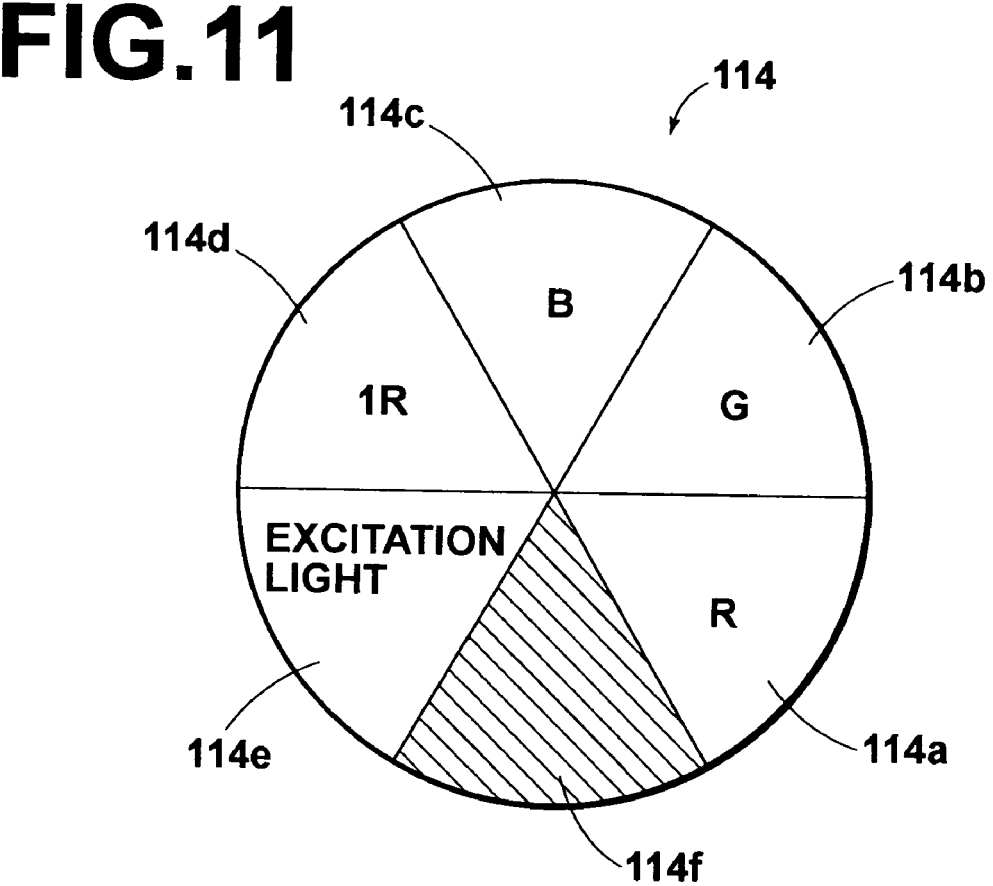
FIG. 11 is a drawing illustrating the configuration of a rotary filter.

FIG. 11 is a drawing illustrating the configuration of the rotary filter 114. As shown in FIG. 11, the rotary filter 114 comprises filter elements 114a, 114b, 114c, 114d, and 114e that respectively pass R-light, G-right, B-light, near infrared light in the wavelength band of 750 nm to 900 nm, exciting light of 410 nm wavelength, and a light shielding element 114f for shielding the light.

By rotating the rotary filter 114, the cycle of irradiation of the R, G, B, near infrared, and excitation light to the living body observation area 9, and the shielding of the light is repeated. Here, only the optical images that have passed through the wide band-pass filter elements 108a of the mosaic filter 108 are detected by the CCD imaging device 106 while the R-light Lr, G-light Lg, B-light Lb, and reference light Ls are irradiated on the living body observation area 9, and all fluorescent images that have passed through the wide band-pass filter elements 108a and narrow band-pass filter elements 108b are detected by the CCD imaging device 106 when the excitation light Le is irradiated on the living body observation area 9.

Here, the rotary filter 114 is rotated by the motor 115 such that the time for irradiating each of the light components to the living body observation area 9 corresponds to a time for a single frame in a TV frame rate (e.g., ⅟₆₀ sec, ⅟₃₀ sec, ⅟₂₅ sec).

The CCD controller 140 outputs an operation control signal for controlling the operation timing of the CCD imaging device 106, and a multiplication factor control signal for controlling the multiplication factor of the charge multiplying section 24. By outputting the multiplication factor control signal having a desired peak value set by the user, the multiplication factor of the charge multiplying section 24 may be controlled. Here, the CCD controller 140 outputs the operation control signal such that the signal charges are read out N times from the CCD imaging device 106 in a single exposure.

The image processing unit 130 includes a signal processing circuit 131 for implementing a predetermined process for a signal obtained by the CCD imaging device 106; an A/D conversion circuit 132 for digitizing the image data obtained by the signal processing circuit 131; an image memory 133 for storing respective image data of respective colors obtained from the reflected images Zr, Zg, and Zb; a fluorescent image memory 135 for respectively storing wide-band fluorescent image data representing a wide-band fluorescent image, and narrow-band fluorescent image data representing a narrow-band fluorescent image obtained from the fluorescent image Ze, which will be described later; image memory 136 for storing reference image data obtained from the reflected image Zs; an image generation circuit 137 for calculating the ratio of the pixel values between the corresponding pixels of the wide-band fluorescent image represented by the wide-band fluorescent image data and the narrow-band fluorescent image represented by the narrow-band fluorescent image data to obtain the calculation results and generating a colored image data representing a colored image by allocating color information to the calculation results in proportion to the value thereof, generating brightness image data representing a brightness image by allocating brightness information to each of the pixels of the reference image represented by the reference image data in proportion to the pixel values thereof, and generating a composite image data representing a fluorescent diagnostic image by combining the colored image data and the brightness image data to be outputted; and video signal processing circuit 134 for converting the respective image data of the three colors outputted from the image memory 133 in a synchronized manner, and the composite image data generated by the image generation circuit 137 into a video signal to be outputted.

The image generation circuit 137 may be an image generation circuit that calculates the ratio of the pixel values between the corresponding pixels of the reference image represented by the reference image data stored in the image memory 136 and the wide-band fluorescent image represented by the wide-band fluorescent image data, or the narrow-band fluorescent image represented by the narrow-band fluorescent image data stored in the fluorescent image memory 135, and generates colored image data representing a colored image by allocating color information to the calculation results in proportion to the value thereof.

Hereinafter, the operation of the endoscope system according to this preferred embodiment will be described. In the endoscope system according to this embodiment, the imaging of the reflected images Zr, Zg, and Zb, imaging of reflected image Zs, and imaging of the fluorescent image Ze are implemented in a time-division mode, and an ordinary image 11 based on the reflected images Zr, Zg, and Zb, and fluorescent diagnostic image 13 based on the reflected image Zs and fluorescent image Ze are displayed on the monitor 200. In order to pick up each of the optical images in a time-division mode, the rotary filter 114 in the illumination unit 110 is rotated to pass the white light radiated from the white light source 111 through the rotary filter 114 to sequentially irradiate the R-light Lr, G-light Lg, B-light Lb, reference light Ls, and excitation light Le on the living body observation area 9.

First, the operation of the system for displaying an ordinary image 11 will be described. The white light radiated from the white light source 111 passes through the filter element 114a of the rotary filter 114 to be turned into the R-light Lr, which is guided through the light guide 101, passed through the illumination optical system 103, and irradiated on the living body observation area 9.

The reflected image Zr represented by the R-light Lr reflected from the living body observation area 9 is converged by the converging lens 105, passed through the excitation light cut filter 104, reflected by the prism 107, passed through the wide band-pass filter elements 108a of the mosaic filter 108, and formed on the CCD imaging device 106.

On the CCD imaging device 106, the reflected image Zr is received by the vertical transfer CCDs 31 of the light receiving section 21, and converted into an electrical signal by photoelectric conversion in proportion to the intensity of the light.

When a predetermined time period corresponding to a time for a single frame in a TV frame rate has elapsed, the rotary filter 114 rotates to switch the filter element to be placed on the light path of the white light radiated from the white light source 111 from the filter element 114a for R-light to the filter element 114b for G-light. During this predetermined time period, the signal charges are read out N times from the storage section 22. Hereinafter, the operation of the system for single reading will be described. First, the signal charges stored in the vertical transfer CCDs 31 are transferred to the vertical transfer CCDs 33 of the storage section 22.

The signal charges transferred to the vertical transfer CCDs 33 of the storage section 22 are vertically transferred in parallel, and sequentially fed into the horizontal transfer CCDs 35 of the horizontal transfer section 23.

In the horizontal transfer section 23, when the signal charges of the pixels of a single row of the storage section are fed into the horizontal CCDs 35, the signal charges are transferred in a horizontal direction to the charge multiplying cells 36 of the sequential charge multiplying section 24. In the charge multiplying cells 36, the signal charges are sequentially transferred as the charges are multiplied based on the multiplication factor control signal. The signal charges outputted from the last charge multiplying cell 36 to the output section 25 located on the right end are converted into a signal voltage in the charge detecting section 37, amplified by an output amplifier 38, and outputted from the output terminal 27 as an output signal.

Thereafter, the signal charges of the next row are transferred from the storage section 22 to the horizontal transfer section 23. By repeating the process described above, the signal charges are read out sequentially from the pixel in the left bottom to rightward, and when the signal charges of that row are read out, signal charges in the next upper row are read out, and then the next. In this way, the signal charges that forms an R-image are read out as an output signal by the single reading. The imaging of the CCD imaging device is implemented in accordance with the operation control signal inputted thereto from the CCD controller 140.

The output signal obtained by the single reading is subjected to the predetermined process at the signal processing circuit 131 of the image processing unit 130, converted into a digital signal at the A/D conversion circuit 132, and stored into the R-image data storage section of the image memory 133. Then, in the image memory 133, the output signals obtained by N times of reading are accumulated, and the R-image data of the accumulated output signal is stored in the storage section of the image memory 133.

Thereafter, G-image data, and B-image data are obtained through the identical process, and respectively stored into the G-image data storage section, and B-image data storage section of the image memory 133.

When the respective image data of the three colors have been stored, these data are outputted in synchronization with the display timing, converted into a video signal in the video signal processing circuit 134, and outputted to the monitor 200 to be displayed as a colored ordinary image 11.

Hereinafter, the operation of the system for displaying the fluorescent diagnostic image 13 will be described. The rotary filter 114 is rotated continuously according to the signal from the controller 150, and the filter element 114d is placed on the light path of the white light radiated from the white light source 111 following the filter element 114c, which causes the reference light Ls of near infrared light to be irradiated on the living body observation area 9.

The reflected image Zs represented by the reference light Ls reflected from the living body observation area 9 is converged by the converging lens 105, passed through the excitation light cut filter 104, reflected by the prism 107, passed through the wide band-pass filter elements 108a of the mosaic filter 108, and formed on the CCD imaging device 106.

The reflected image Zs received by the CCD imaging device 106 is converted into an electrical signal through photoelectric conversion, and inputted to the image processing unit 130 in the same manner as described above. The electrical signal inputted to the image processing unit 130 is subjected to the predetermined process at the signal processing circuit 131, converted into a digital signal at the A/D conversion circuit 132, and stored into the image memory 136 as the reference image data.

Hereinafter, the operation of the system for imaging the fluorescent image Ze developed by the excitation light will be described. The rotary filter is rotated continuously according to the signal from the controller 150, and the filter element 114e is placed on the light path of the white light radiated from the white light source 111 following the filter element 114d, which causes the excitation light Le to be irradiated on the living body observation area 9.

The fluorescent image Ze developed in the living body observation area 9 by the irradiation of the excitation light Le is converged by the converging lens 105, passed through the excitation light cut filter 104, reflected by the prism 107, passed through the wide band-pass filter elements 108a and narrowband-pass filter elements 108b of the mosaic filter 108, and formed on the CCD imaging device 106.

The fluorescent image received by the CCD imaging device 106 is converted into electrical signals through photoelectric conversion implemented respectively for the pixels corresponding to the wide band-pass filter elements, and for the pixels corresponding to the narrow band-pass filter elements, and inputted to the image processing unit 130 in the same manner as described above. The electrical signals inputted to the image processing unit 130 are subjected to the predetermined process at the signal processing circuit 131, converted into digital signals at the A/D conversion circuit 132, and stored into the fluorescent image memory 135 as wide-band fluorescent image data and narrow-band fluorescent image data.

When the wide-band fluorescent image data and narrow-band fluorescent image data have been obtained, the image generation circuit 137 calculates the ratio of the signal strengths between the corresponding pixels of the wide-band fluorescent image data and narrow-band fluorescent image data to obtain colored image data by allocating the color information to the ratio calculated, obtains brightness image data by allocating brightness information to the signal strength of the reference image data, and generates a combined image data by combining these data, which is outputted to the video signal processing circuit 134. The video signal processing circuit 134 converts the combined image data into a video signal, which is outputted to the monitor 200. The monitor 200 displays the fluorescent diagnostic image 13 of a pseudo-colored image.

The fluorescent diagnostic image 13 is displayed as a pseudo-colored image that changes the displayed colors in accordance with the changes in relative ratio of the signal strengths between the wide-band fluorescent image data and narrow-band fluorescent image data, and changes the brightness in accordance with the signal strength of the reference image data. Pseudo-colors which are clearly distinguishable on the display between the fluorescent light emitted from a normal tissue and that emitted from a diseased tissue may be set. For example, the fluorescent light emitted from a normal tissue may be displayed in white, while the fluorescent light emitted from a diseased tissue may be displayed in pink or other colors, which allows the observer to readily recognize the diseased tissue. Further, the brightness of the displayed image changes in accordance with the signal strength of the reference image data, so that a fluorescent diagnostic image having irregularities and a sense of distance on the living body observation area 9 may be displayed.

As described above, in this preferred embodiment, the endoscope system has a CCD imaging device with each of the pixels having a full well size equivalent to 1/M of the number of electrons required by the system, i.e., 1/M of the number of electrons corresponding to the maximum amount of light which may be received by the individual pixel determined by the technical specifications of the system, implements N times of reading in every prescribed read time, and is adapted to satisfy the relation of $nd(1-1/M) > nr^2(N^2-1)$. Here, the dark noise may be reduced when the full well size is small, but if the light volume of the illumination light is large, the signal charge is saturated. As opposed to this, the saturation of the signal charges may be avoided by the multi-reading as in this embodiment. But, if the amount of readout noise is large, when the signal charges obtained by the multi-reading are accumulated, the noise contained in the output signal is increased, even if the amount of dark noise is small.

This preferred embodiment uses a charge multiplying imaging device 106, so that the readout noise may be reduced. In addition this embodiment is adapted to satisfy the relation of $nd(1-1/M) > nr^2(N^2-1)$, so that the noise, including dark noise contained in the output signal may be reduced to less than that contained in the output signal obtained by the single reading in each exposure using a CCD imaging device with each of the pixels having a full well size equivalent to the number of electrons required by the system. Accordingly, the output signal of reduced noise may be obtained without cooling the CCD imaging device 106, allowing a high quality ordinary image 11, and fluorescent diagnostic image 13 to be displayed on the monitor 200.

Assuming that the number of electrons corresponding to the maximum amount of light which may be received by the single pixel determined by the technical specifications of the system is 60,000 electrons, and the full well size of the CCD imaging device 106 is ⅕ of 60,000 electrons with five times of reading, then we have $\frac{1}{30} nd > nr^2$, derived from the formula, $nd(1-1/M) > nr^2(N^2-1)$.

Generally, the dark noise of the CCD imaging device with a full well size of 60,000 electrons is 2,000 electrons at the device temperature of 55° C., so that the noise contained in the output signal may be reduced when the readout noise is about 8.2 electrons or less, which is derived from the formula, $\frac{1}{30} nd > nr^2$. In an imaging device having extremely low readout noise like the charge multiplying CCD imaging device, it is possible to reduce the readout noise to one electron or less. By reducing the readout noise to such a small amount, the noise contained in the output signal may be reduced.

Generally, the full well size of a CCD imaging device is several tens of thousand electrons, and the physical size of the pixel is several $\mu m \times$ several $\mu m$. If the full well size is reduced to 1/M as in this preferred embodiment, the pixel size of the CCD imaging device may be reduced to 1/M compared with a CCD imaging device with each of the pixels having a full well size corresponding to the number of electrons required by the apparatus, resulting in that the physical size of the imaging device may be reduced to $1/M^2$. Thus, the physical size of the CCD imaging device may be reduced, and the application of the imaging device of the present invention to an endoscope system allows the use of a thinner endoscope.

Further, the reduced physical size of the CCD imaging device may increase the number of CCD imaging devices manufactured from a single wafer, thereby the production efficiency may be increased.

In the preferred embodiment described above, the present invention is applied to an endoscope system, but it may also be applied to other imaging apparatuses, in addition to the endoscope system.

For example, the imaging device mounted on a cell phone with a camera, and other portable terminals including a PDA with a camera must be operable under the harsh environment of temperatures ranging from a low to high temperatures, and must be compact and lightweight from the view point of mobility. In addition, there is a demand for an imaging device with higher pixel density and sensitivity. If the ambient temperature of the portable terminal is 30° C., the temperature of the imaging device goes up as high as 60° C., so that the dark noise is increased, and the graininess of the image obtained is degraded. Here, it may be possible to cool the imaging device using a cooling mechanism, such as a cooling fan, or Peltier device, but the provision of the cooling mechanism results in an increased size, and reduced operating time of the portable terminal due to power consumption of the battery by the cooling mechanism.

Accordingly, application of the imaging apparatus of the present invention to the portable terminal allows the user to obtain a low-noise and high-quality image without any cooling mechanism. For example, when the full well size of the CCD imaging device used for the imaging apparatus is reduced to ¼ of the number of electrons corresponding to the maximum amount of light which may be received by the individual pixel determined by the technical specifications of the portable terminal, and the reading frequency of the imaging apparatus is set at four times in each exposure, the imaging apparatus may obtain a lower-noise and higher-quality image without changing the amount of output signal obtained by each of the pixels compared with an imaging apparatus that uses a CCD imaging device with a full well size equivalent to the number of electrons corresponding to the maximum amount of light which may be received by the individual pixel determined by the technical specifications of the portable terminal. More specifically, when the device temperature is 60° C., and the readout noise is 0.7 e⁻, as shown in FIG. 8, the noise generated by the imaging device is reduced to approximately ½ in the case where N=M=4 compared with the case where N=M=1, so that the noise reduction effect equivalent to that achieved by cooling the device approximately by 8° C., which is derived from the Formula (14) above, may be obtained.

The invention claimed is:

1. An imaging apparatus comprising:
    a solid-state imaging means having a charge multiplying section for multiplying signal charges obtained through imaging by each of the pixels of said imaging means having a full well size equivalent to 1/M of the number of electrons corresponding to a maximum amount of light which may be received by the individual pixel determined by the technical specifications of said apparatus; and
    a reading means for reading out said signal charges from said solid-state imaging means N times in a predetermined time period,
    wherein said apparatus is adapted to satisfy the following relation:

$$nd(1-1/M) > nr^2(N^2-1)$$

where nd is the dark noise, and nr is the readout noise when signal charges are read out once in said predetermined time period from a reference solid-state imaging device with each of the pixels having a full well size equivalent to said number of electrons.

2. An imaging apparatus according to claim 1, wherein said apparatus is further adapted to satisfy the following relation:

$$Nr^2/nd = 1/(2NM^2).$$

3. An imaging apparatus according to claim 1, wherein said solid-state imaging device is a frame transfer CCD imaging device.

4. An image obtaining apparatus comprising:
    a irradiation means for guiding illumination light to an area under test, and irradiating said light thereon; and
    an imaging apparatus of claim 1 for picking up an optical image originating from said area by the irradiation of said illumination light from said irradiation means.

5. An image obtaining apparatus according to claim 4, wherein said apparatus takes the form of an endoscope having an insertion section comprising a part or whole of said irradiation means and imaging apparatus to be inserted into a living body.

6. An image obtaining apparatus according to claim 5, wherein said solid-state imaging device is provided at the leading end of said insertion section.

7. An image obtaining apparatus according to claim 6, wherein said solid-state imaging device has a mosaic filter comprising microscopic band-pass filter elements combined in mosaic.

8. An image obtaining apparatus according to claim 4, wherein said illumination light comprises R-light, G-light, B-light, IR-light and excitation light.

9. An image obtaining apparatus according to claim 8, wherein said irradiation means is a means for obtaining said R-light, G-light, B-light, IR-light and excitation light by passing white light through a rotary filter having filter elements that pass said light components having the wavelength band of R, G, B, IR, and excitation light respectively.

10. An image obtaining apparatus according to claim 9, wherein said irradiation means has a rotating means for rotating said rotary filter such that each of said filter elements passes each of said light components for a time corresponding to a time for a single frame in a TV frame rate.

* * * * *